United States Patent [19]
Manogue et al.

[11] Patent Number: 5,892,135
[45] Date of Patent: *Apr. 6, 1999

[54] PROCESS FOR THE PRODUCTION OF TRIFLUOROETHYLENE

[75] Inventors: William H. Manogue, Newark; V.N. Mallikarjuna Rao, Wilmington, both of Del.

[73] Assignee: E. I. du Pont de Nemours and Company, Wilmington, Del.

[ * ] Notice: This patent issued on a continued prosecution application filed under 37 CFR 1.53(d), and is subject to the twenty year patent term provisions of 35 U.S.C. 154(a)(2).

[21] Appl. No.: 911,118

[22] Filed: Aug. 14, 1997

Related U.S. Application Data

[60] Provisional application No. 60/024,313, Aug. 23, 1996.

[51] Int. Cl.⁶ .................................................. C07C 17/25
[52] U.S. Cl. ............................................................ 570/156
[58] Field of Search ............................................... 570/156

[56] References Cited

U.S. PATENT DOCUMENTS

| | | | |
|---|---|---|---|
| 2,704,775 | 3/1955 | Clark | 570/156 |
| 2,802,887 | 8/1957 | Miller et al. | 570/156 |
| 2,900,423 | 8/1959 | Smith | 570/156 |
| 5,043,491 | 8/1991 | Webster et al. | 570/157 |
| 5,057,634 | 10/1991 | Webster et al. | 50/157 |
| 5,068,472 | 11/1991 | Webster et al. | 570/157 |
| 5,089,454 | 2/1992 | Lerot et al. | 502/226 |
| 5,283,379 | 2/1994 | Saiki et al. | 570/156 |
| 5,315,045 | 5/1994 | Berthe et al. | 570/156 |

*Primary Examiner*—Alan Siegel

[57] ABSTRACT

A process for the production of trifluoroethylene (i.e., $CF_2$=CHF or HFC-1123) is disclosed. The process involves contacting (in the vapor phase) at least one halogenated ethane of the formula $CF_3CClFX$ (where X is H, Cl or F) with hydrogen in the presence of a catalyst including at least one component selected from elemental metals, metal oxides, metal halides and metal oxyhalides. The metal of the component is ruthenium, copper, nickel, and/or chromium and the halogen of the halides and the oxyhalides is fluorine and/or chlorine.

9 Claims, No Drawings

PROCESS FOR THE PRODUCTION OF TRIFLUOROETHYLENE

This application claims the priority benefit of U.S. Provisional application Ser. No. 60/024,313, filed Aug. 23, 1996.

FIELD OF THE INVENTION

This invention relates to a process for the production of trifluoroethylene, and more particularly, to a catalytic process for the preparation of trifluoroethylene from saturated halogenated hydrocarbons.

BACKGROUND

Trifluoroethylene (i.e., $CF_2=CHF$ or HFC-1123) is a useful monomer for the preparation of fluorocarbon polymers.

HFC-1123 can be produced from $CCl_2FCClF_2$ (CFC-113) by reaction with hydrogen in the presence of a catalyst comprising palladium and at least one other metal selected from gold, tellurium, antimony, bismuth and arsenic (U.S. Pat. No. 5,283,379). HFC-1123 can also be prepared from $CF_2=CClF$ (CFC-1113) by reaction with hydrogen in the presence of a catalyst comprising palladium or platinum on a magnesium oxide carrier (U.S. Pat. No. 5,089,454). A product of over-hydrogenolysis from both CFC-113 and CFC-1113 is $CH_2FCHF_2$ (HFC-143). There is continuing interest in developing efficient processes for the manufacture of HFC-1123.

SUMMARY OF THE INVENTION

This invention provides a process for the production of trifluoroethylene (i.e., $CF_2=CHF$ or HFC-1123). The process comprises contacting in the vapor phase at least one halogenated ethane of the formula $CF_3CClFX$ where X is selected from the group consisting of H, Cl and F, with hydrogen in the presence of a catalyst comprising at least one component selected from the group consisting of elemental metals, metal oxides, metal halides and metal oxyhalides; wherein the metal of said component is selected from ruthenium, copper, nickel, chromium and mixtures thereof and the halogen of said halides and said oxyhalides is selected from fluorine, chlorine and mixtures thereof.

DETAILED DISCUSSION

The present invention provides a process for the manufacture of trifluoroethylene by contacting at least one halogenated ethane selected from the group consisting of 2-chloro-1,1,1,2-tetrafluoroethane (i.e., $CHClFCF_3$ or HCFC-124), 2,2-dichloro-1,1,1,2-tetrafluoroethane (i.e., $CCl_2FCF_3$ or CFC-114a) and chloropentafluoroethane (i.e., $CClF_2CF_3$ or CFC-115) with hydrogen. The contact is in the vapor phase and in the presence of selected hydrogenation catalysts. Preferred processes include those which use the halogenated ethane HCFC-124 and/or the halogenated ethane CFC-114a as starting material. The more preferred starting material is HCFC-124. It is noted that CFC-114 (i.e., $CClF_2CClF_2$) and HCFC-124a (i.e., $CClF_2CHF_2$) can also be employed a starting materials under conditions where they isomerize (to CFC-114a and HCFC-124, respectively). Catalysts which facilitate such isomerization include catalysts comprising aluminum halides (e.g., $AlF_3$) or aluminum oxyhalides.

The present invention involves the use of advantageously catalytic components employing ruthenium, copper, nickel and/or chromium. Suitable components include elemental metals such as ruthenium and ruthenium-copper mixtures; halides such as CuF, CuCl, CuClF, $NiF_2$, $NiCl_2$, NiClF, $CrF_3$, $CrCl_3$, $CrCl_2F$ and $CrClF_2$; oxides such as CuO, NiO, and $Cr_2O_3$; and oxyhalides such as copper oxyfluoride and chromium oxyfluoride. Oxyhalides may be produced by conventional procedures such as, for example, halogenation of metal oxides.

The catalysts of this invention may contain other components, some of which are considered to improve the activity and/or longevity of the catalyst composition. Preferred catalysts include catalysts which are promoted with compounds of molybdenum, vanadium, tungsten, silver, iron, potassium, cesium, rubidium, barium or combinations thereof. Also of note are chromium-containing catalysts which further contain zinc and/or aluminum or which comprise copper chromite.

The catalyst may be supported or unsupported. Supports such as metal fluorides, alumina and titania may be advantageously used. Particularly preferred are supports of fluorides of metals of Group IIB, especially calcium. A preferred catalyst consists essentially of copper, nickel and chromium oxides (each of said oxides being preferably present in equimolar quantities) preferably promoted with potassium salt, on calcium fluoride.

An especially preferred catalyst contains proportionally about 1.0 mole CuO, about 0.2 to 1.0 mole NiO, about 1 to 1.2 moles $Cr_2O_3$ on about 1.3 to 2.7 moles $CaF_2$, promoted with about 1 to 20 weight %, based on the total catalyst weight, of an alkali metal selected from K, Cs, and Rb (preferably K). When K is the promoter, the preferred amount is from about 2 to 15 weight % of the total catalyst.

This catalyst can be prepared by coprecipitating, from an aqueous medium, salts of copper, nickel and chromium (and optionally aluminum and zinc), with and preferably on calcium fluoride; washing, heating and drying the precipitate. An alkali metal compound (e.g., KOH, KF or $K_2CO_3$) is then deposited on the dried precipitate, followed by calcination to convert the copper, nickel and chromium to the respective oxides. Any soluble copper, nickel and chromium compound may be used, but the fluorides, chlorides and nitrates are preferred, with the nitrates being especially preferred. Alternatively, promoters such as KOH, KF and $K_2CO_3$ may be added prior to co-precipitation.

Another group of catalysts which may be used for the conversion of $CF_3CClFX$ contains proportionally about 1.0 mole CuO, about 0.2 to 1.0 mole NiO, about 1 to 1.2 moles $Cr_2O_3$, about 0.4 to 1.0 mole $MoO_3$, and about 0.8 to 4.0 mole $CaF_2$, optionally promoted with at least one compound from the group consisting of $MgF_2$, $MnF_2$, and $BaF_2$. Pd or $WO_3$ may also be present.

Another preferred group of catalysts are those comprising ruthenium. Of note are supported ruthenium catalysts. Examples include ruthenium supported on aluminum fluoride, chromium fluorides, rare earth fluorides, or divalent metal fluorides.

The catalyst may be granulated, pressed into pellets, or shaped into other desirable forms. The catalyst may contain additives such as binders and lubricants to help insure the physical integrity of the catalyst during granulating or shaping the catalyst into the desired form. Suitable additives include carbon and graphite. When binders and/or lubricants are added to the catalyst, they normally comprise about 0.1 to 5 weight percent of the weight of the catalyst.

The catalyst may be activated prior to use by treatment with hydrogen, air, or oxygen at elevated temperatures. After use for a period of time in the process of this invention, the activity of the catalyst may decrease. When this occurs, the catalyst may be reactivated by treating it with hydrogen, air or oxygen, at elevated temperature in the absence of organic materials.

The molar ratio of hydrogen to $CF_3CClFX$ typically ranges from about 0.5:1 to about 30:1, and is preferably within the range of about 1:1 to about 24:1.

The process of the present invention is suitably conducted at a temperature in the range of from about 200° C. to 500° C., preferably from about 325° C. to about 425° C. The contact time of reactants with the catalyst bed is typically from about 0.1 seconds to about 2.0 minutes, and is preferably from about 10 seconds to 90 seconds.

Atmospheric or superatmospheric pressures may suitably be employed.

The reaction products may be separated by conventional techniques such as distillation. In accordance with this invention, when $CF_3CHClF$ is contacted with catalyst, the reaction temperature, pressure and contact time may be controlled such that the major (selectivity greater than 50%) reaction product is trifluoroethylene. Other products which can be isolated and are useful are tetrafluoroethane (i.e., $CH_2FCF_3$ or HFC-134a), a refrigerant, and vinylidene fluoride (i.e., $CH_2=CF_2$ or HFC-1132a), a monomer for making fluorinated polymers.

The process of this invention can be carried out readily in the vapor phase using well known chemical engineering practice.

The reaction zone and its associated feed lines, effluent lines and associated units should be constructed of materials resistant to hydrogen fluoride and hydrogen chloride. Typical materials of construction, well-known to the fluorination art, include stainless steels, in particular of the austenitic type, the well-known high nickel alloys, such as Monel® nickel-copper alloys, Hastelloy® nickel-based alloys and, Inconel® nickel-chromium alloys, and copper-clad steel. Silicon carbide is also suitable for reactor fabrication.

Without further elaboration, it is believed that one skilled in the art can, using the description herein, utilize the present invention to its fullest extent. The following preferred specific embodiments are to be construed as illustrative, and not as constraining the remainder of the disclosure in any way whatsoever.

EXAMPLES

Catalyst Preparation for Examples 1–5

Aqueous calcium nitrate (2.7 moles) is mixed with aqueous potassium fluoride (5.4 moles), heated and stirred briefly at 100° C. to form a slurry of $CaF_2$. To this slurry is added copper nitrate (1 mole), nickel nitrate (1 mole) and chromium nitrate (1 mole) as solids. The slurry is stirred at 70° to 80° C. until the salts, other than $CaF_2$, dissolve. This is followed by adding 0.1 mole of aqueous potassium hydroxide over 1 hour and boiling the mixture briefly. The slurry is cooled to 40° to 50° C. and filtered. The solid is washed exhaustively to reduce the potassium content to an undetectable level. After drying, potassium hydroxide is added as a solution in quantities sufficient to provide a catalyst containing 9 weight % potassium. After drying again, the catalyst is calcined at 600° C. for 8 to 16 hours, then granulated and screened to 1 to 2 mm particles. The catalyst is mixed with 1 to 5 wt % "Sterotex" powdered lubricant (registered trademark of Capital City Products Co., Columbus Ohio, division of Stokely-Van Camp, for its edible hydrogenated vegetable oil) to give ⅛"×⅛" (3.2 mm×3.2 mm) cylindrical pellets from a Stokes tablet machine. This catalyst is used as described in Examples 1–5.

General Procedure for Product Analysis for Examples 1–4

The products leaving the reactor were analyzed on line using a gas chromatograph. The column consisted of a 20' (6.1 m)×⅛"(3.2 mm) s/s tube containing Krytox™ perfluorinated polyether on an inert support. Helium was used as the carrier gas. The product analyses are reported in mole %.

| Legend | |
|---|---|
| 124 is $CHClFCF_3$ | 143a is $CH_3CF_3$ |
| 1132a is $CH_2=CF_2$ | 1123 is $CHF=CF_2$ |
| 134a is $CH_2FCF_3$ | 1122 is $CHCl=CF_2$ |

CT is the contact time in minutes at reaction conditions, based on catalyst volume Conv. is starting material converted Selectivities are based upon the mole fraction of starting material converted

EXAMPLE 1

A 15" (38.1 cm)×¼" (0.64 cm) O.D. Inconel™ 600 nickel alloy U-tube reactor was charged with catalyst (8.3 g, 6 mL) pellets prepared substantially in accordance with the Catalyst Preparation above. The catalyst was treated with 50 sccm ($8.3 \times 10^{-7}$ m³/s) air at 525° C. for 1.0 hours and at 400° C. for 0.33 hours, followed by purging with 150 sccm ($2.5 \times 10^{-6}$ m³/s) nitrogen at 400° C. for 5 hours. $CHClFCF_3$ and $H_2$ were contacted with the catalyst at 300° to 425° C., 0 psig (101 kPa) and with a molar ratio of $H_2:CHClFCF_3$ of 1:1. Results of the reaction for 23 hours are shown in the

TABLE 1

| Run No. | Temp. °C. | CT min. | % Conv. 124 | Selectivities, % | | | |
|---|---|---|---|---|---|---|---|
| | | | | 1132a | 1123 | 134a | 1122 |
| 1 | 300 | 1.27 | 34 | 4.2 | 67 | 24 | 3.4 |
| 2 | 325 | 1.21 | 53 | 4.3 | 74 | 15 | 3.9 |
| 3 | 350 | 1.17 | 74 | 6.4 | 78 | 10 | 2.5 |
| 4 | 375 | 1.12 | 83 | 7.4 | 82 | 6 | 1.2 |
| 5 | 400 | 1.08 | 91 | 6.9 | 83 | 5 | 0.5 |
| 6 | 425 | 1.04 | 84 | 7.9 | 82 | 5 | 0.5 |

EXAMPLE 2

A 15" (38.1 cm)×⅜" (0.95 cm) O.D. Inconel™ 600 nickel alloy U-tube reactor was charged with the catalyst (21.7 g, 18 mL) pellets prepared substantially in accordance with the Catalyst Preparation above. Following prior use of the catalyst, the catalyst was treated with air at 300° to 400° C. for 10 hours, followed by purging with nitrogen at 400° C. for 6 hours. The catalyst was then treated with mixture of 50 sccm ($8.3 \times 10^{-7}$ m³/s) hydrogen and 100 sccm ($1.7 \times 10^{-6}$ m³/s) nitrogen at 400° to 450° C. for 1.5 hours and finally purging with nitrogen while cooling the catalyst bed to 300° C. $CHClFCF_3$ and $H_2$ were contacted with the catalyst at 300° to 340° C., 0 psig (101 kPa) and with a molar ratio of $H_2:CHClFCF_3$ of 4:1. Results of the reaction are shown in the Table 2.

TABLE 2

| Run No. | Temp. °C. | CT min. | % Conv. 124 | Selectivities, % | | |
|---|---|---|---|---|---|---|
| | | | | 1132a | 1123 | 134a |
| 1 | 300 | 0.5 | 30 | 4.6 | 68 | 19 |
| 2 | 320 | 0.5 | 45 | 7.5 | 72 | 15 |
| 3 | 340 | 0.5 | 65 | 7.6 | 77 | 10 |

EXAMPLE 3

The same reactor and catalyst were used as used in Example 2. $CHClCF_3$ and $H_2$ were contacted with the catalyst at 330° to 350° C., 30 psig (308 kPa) and with a molar ratio of $H_2$:$CHClCF_3$ of 4:1. Results of the reaction are shown in the Table 3.

TABLE 3

| Run No. | Temp. °C. | CT min. | % Conv. 124 | Selectivities, % | | |
|---|---|---|---|---|---|---|
| | | | | 1132a | 1123 | 134a |
| 1 | 330 | 0.5 | 45 | 6.5 | 71 | 16 |
| 2 | 330 | 1.0 | 58 | 5.0 | 73 | 15 |
| 3 | 340 | 0.5 | 56 | 5.7 | 72 | 15 |
| 4 | 340 | 1.0 | 67 | 4.8 | 74 | 14 |
| 5 | 350 | 0.5 | 65 | 5.8 | 74 | 13 |
| 6 | 350 | 1.0 | 73 | 4.8 | 75 | 13 |

EXAMPLE 4

The same reactor and catalyst were used as used in Example 3. The catalyst was purged with nitrogen at 200° C. for 45 minutes. The catalyst was then treated with 50 sccm ($8.3 \times 10^{-7}$ m$^3$/s) air at 300° C. for 3.5 hours, at 350° C. for 5 hours, at 400° C. for 6 hours, followed by purging with nitrogen at 400° C., for 6 hours. $CHClCF_3$ and $H_2$ were contacted with the catalyst at 340° to 380° C., 300 psig (2169 kPa) and with a molar ratio of $H_2$:$CHClCF_3$ of 24:1. The results of the reaction are shown in the Table 4. The potassium-promoted catalyst sample used in this example had been in use for a total of over 600 hours (not including regeneration time) after completion of the runs in Table 4.

TABLE 4

| Run No. | Temp. °C. | CT min. | % Conv 124 | Selectivities, % | | | | |
|---|---|---|---|---|---|---|---|---|
| | | | | 1132a | 1123 | 143a | 134a | 1122 |
| 1 | 340 | 0.47 | 77 | 2.6 | 61 | 2.4 | 26 | 1.1 |
| 2 | 340 | 0.94 | 87 | 2.5 | 54 | 2.6 | 31 | 0.9 |
| 3 | 350 | 0.23 | 59 | 4.5 | 59 | 2.5 | 26 | 1.1 |
| 4 | 360 | 0.45 | 78 | 4.4 | 58 | 2.5 | 26 | 1.2 |
| 5 | 360 | 0.23 | 59 | 5.0 | 60 | 2.6 | 24 | 1.1 |
| 6 | 350 | 0.24 | 46 | 4.8 | 60 | 2.5 | 26 | 1.1 |
| 7 | 350 | 0.92 | 75 | 3.6 | 59 | 2.3 | 26 | 1.1 |
| 8 | 355 | 0.46 | 56 | 4.1 | 63 | 2.3 | 22 | 1.1 |
| 9 | 365 | 0.45 | 53 | 3.6 | 70 | 1.5 | 16 | 1.1 |
| 10 | 380 | 0.45 | 45 | 2.7 | 79 | 0.0 | 9 | 1.1 |

Experimental Procedure for Examples 5–7

The reaction of HCFC-124 and $H_2$ was carried out using a multi-port vapor phase reactor. A nickel cylinder was bored out to hold eight individual catalyst tubes. Each tube, when connected with the rest of the reactor system, had its own nitrogen purge supply. Each of the catalyst tubes could be charged with catalyst prior to sealing the nickel cylinder and wrapping it in insulation. Thermocouples were placed on the surface of the cylinder and in an interior location within the cylinder to monitor temperature.

HCFC-124 and $H_2$ were fed to the reactor system using a Tylan® 280SA mass flow meter. The mass flow meter was calibrated using a J&W Scientific ADM1000 Flow Meter.

For each example, the catalyst was used as received without pre-treatment for a nitrogen purge. After 2 hours of run time, the products leaving the reactor were analyzed on-line using a Hewlett-Packard® 5880 gas chromatograph. The column used was a 20'×⅛" stainless steel tube containing Krytox™ perfluorinated polyether on an inert support. Helium was used as the carrier gas. Product analyses are listed in mole %. Selectivity is based upon the mole % of HCFC-124 converted.

EXAMPLE 5

A 3" (7.6 cm)×¼" (0.64 cm) O.D. Inconel™ 600 nickel alloy tube was charged with 1.11 grams (0.9 cc) of catalyst prepared substantially in accordance with the Catalyst Preparation above and then crushed to about 20–30 mesh. Hydrogen was fed at 2 sccm and HCFC- 124 was fed at 1 sccm (corresponding to a contact time of about 0.3 min). The reactor temperature was set at 400° C. After 2 hours, the conversion of HCFC-124 was 39% and the selectivity to HFC-1123 was 85%.

EXAMPLE 6

Catalyst used was 2% ruthenium on $EuF_3$. The catalyst was prepared by impregnating $EuF_3$ with a solution of $RuCl_3$, and reducing with $H_2$ at 300° C. The particle size was about 20–30 mesh. 1.27 grams (0.86 cc) of catalyst was charged into a tube as described in Example 5. Results of the reaction are shown in Table 5. $H_2$ and HCFC-124 feed rates were varied. The reactor was set at 350° C.

TABLE 5

| Temp (°C.) | 124 Flow (sccm) | $H_2$ Flow (sccm) | Conversion HCFC-124 | Selectivity 1123 |
|---|---|---|---|---|
| 350 | 10.0 | 5.0 | 14.2% | 61.7% |
| 350 | 5.0 | 5.0 | 21.4% | 55.5% |
| 350 | 5.0 | 2.5 | 16.2% | 53.6% |

EXAMPLE 7

Example 6 was substantially repeated except that the catalyst used was Ru-$CrF_3$ prepared by collapsing a $(NH_3)_6RuCrF_6$ composition (see U.S. patent application Ser. No. 60/007,734 and PCT International Publication No. WO 7/19751). 0.74 grams (0.86 cc) of catalyst was charged into a tube as described in Example 5. $H_2$ and HCFC-124 feed rates, as well as the reactor temperatures, were varied. Results of the reaction are shown in Table 6.

TABLE 6

| Temp (°C.) | 124 Flow (sccm) | H2 Flow (sccm) | Conversion HCFC-124 | Selectivity 1123 |
|---|---|---|---|---|
| 300 | 5 | 20 | 56.4% | 21.6% |
| 300 | 5 | 5 | 55.7% | 23.2% |
| 300 | 5 | 2.5 | 45.1% | 32.1% |
| 300 | 10 | 5 | 35.8% | 35.0% |
| 325 | 10 | 5 | 27.2% | 74.9% |
| 300 | 10 | 5 | 28.5% | 88.3% |

We claim:

1. A process for the production of trifluoroethylene, comprising:

contacting in the vapor phase at least one halogenated ethane of the formula $CF_3CClFX$ where X is selected from the group consisting of H, Cl and F, with hydrogen in the presence of a catalyst comprising at least one component selected from the group consisting of elemental metals, metal oxides, metal halides and metal oxyhalides; wherein the metal of said component is selected from ruthenium, copper, nickel, chromium and mixtures thereof and the halogen of said halides and said oxyhalides is selected from fluorine, chlorine and mixtures thereof.

2. The process of claim 1 wherein halogenated ethane selected from the group consisting of $CF_3CHClF$, $CF_3CCl_2F$ and mixtures thereof is used as starting material.

3. The process of claim 2 wherein the starting material is $CF_3CHClF$.

4. The process of claim 3 wherein the catalyst contains proportionally about 1.0 mole CuO, about 0.2 to 1.0 mole NiO, about 1 to 1.2 moles $Cr_2O_3$ on about 1.3 to 2.7 moles $CaF_2$, and is promoted with about 1 to 20 weight %, based on the total catalyst weight, of an alkali metal selected from K, Cs, and Rb.

5. The process of claim 4 wherein the catalyst is promoted with from about 2 to 15 weight % K, based on the total catalyst weight.

6. The process of claim 3 wherein the catalyst contains proportionally about 1.0 mole CuO, about 0.2 to 1.0 mole NiO, about 1 to 1.2 moles $Cr_2O_3$, about 0.4 to 1.0 mole $MoO_3$, and about 0.8 to 4.0 mole $CaF_2$.

7. The process of claim 6 wherein the catalyst is promoted with at least one compound selected from the group consisting of $MgF_2$, $MnF_2$, and $BaF_2$.

8. The process of claim 3 wherein the catalyst comprises ruthenium.

9. The process of claim 3 wherein the catalyst consisting essentially of copper, nickel and chromium oxides, promoted with potassium salt, on calcium fluoride.

* * * * *